United States Patent [19]

Delay et al.

[11] Patent Number: 4,670,109
[45] Date of Patent: Jun. 2, 1987

[54] PROCESS FOR THE PREPARATION OF ISOXAZOLES

[75] Inventors: François Delay, Carouge; Michel Joyeux, Petit-Lancy, both of Switzerland

[73] Assignee: Firmenich SA, Geneva, Switzerland

[21] Appl. No.: 815,855

[22] Filed: Jan. 3, 1986

[30] Foreign Application Priority Data

Jan. 25, 1985 [CH] Switzerland ............................ 340/85

[51] Int. Cl.$^4$ ................................................ C25C 00/00
[52] U.S. Cl. .................................... 204/59 R; 204/72; 204/78; 204/79; 548/247
[58] Field of Search ............... 548/247; 204/59 R, 78, 204/72, 79

[56] References Cited

U.S. PATENT DOCUMENTS

| | | | |
|---|---|---|---|
| 4,149,941 | 4/1979 | Mitzlaff et al. | 204/78 |
| 4,233,121 | 11/1980 | Szebenyi | 204/78 |
| 4,297,181 | 10/1981 | Shono | 204/78 |
| 4,336,202 | 6/1982 | Torii et al. | 204/59 R |
| 4,482,491 | 11/1984 | Torii et al. | 204/72 |
| 4,525,304 | 6/1985 | Hall et al. | 204/78 |
| 4,599,151 | 7/1986 | Torii et al. | 204/59 R |
| 4,600,478 | 7/1986 | Stutts | 204/79 |

FOREIGN PATENT DOCUMENTS 553207  8/1974  Switzerland .

OTHER PUBLICATIONS

Ogumi et al., Electrochimica Acta, 30 (1985) pp. 121–124.
Noda et al., Tetrahedron Letters, 22 (1981) #34, pp. 3247–3248.
Tabakovic et al., Electrochimica Acta, vol. 21, (1976), pp. 621–626.
Begley et al., J. Chem. Soc. (Perkins I) 1974, pp. 2633–2637.

Primary Examiner—Arthur P. Demers
Attorney, Agent, or Firm—Pennie & Edmonds

[57] ABSTRACT

Process for the preparation of isoxazoles by anodic oxidation of alpha,beta-unsaturated oximes, both in heterogeneous and homogeneous phase.

7 Claims, No Drawings

PROCESS FOR THE PREPARATION OF ISOXAZOLES

SUMMARY OF THE INVENTION

The present invention relates to a process for the preparation of isoxazoles of formula

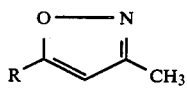
(I)

wherein R represents a linear or branched, saturated or unsaturated aliphatic radical, or a substituted or unsubstituted cycloaliphatic or aromatic radical, which process comprises subjecting to an anodic oxidation either a. a two-layer heterogeneous mixture consisting of
  (i) a solution of an alpha,beta-unsaturated oxime of formula

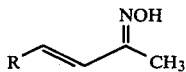
(II)

wherein symbol R possesses the meaning given above, in tetrahydrofurane, and
  (ii) a solution of potassium iodide and sodium bicarbonate in water; or
b. a homogeneous mixture consisting of a solution of said oxime of formula (II), sodium iodide and sodium bicarbonate in methanol.

BACKGROUND OF THE INVENTION

The synthesis of isoxazolic derivatives was thoroughly studied in the past and several methods for preparing the said compounds are known and described in the scientific literature [cf e.g.: Ber., 28,2540 (1895); idem 36,3665 (1903); Compt. Rend., 137,795 (1903); J. Am. Chem. Soc., 49, 2078 (1927); Gazz. Chim. Ital., 70,676 (1940); idem, 72,99 (1942); idem, 76,148 (1946)]. The methods described in the aforementioned references can be distinguished depending on whether they relate to syntheses achieved by 1. reacting 1,3-dicarbonyl compounds with hydroxylamine in accordance with the following scheme:

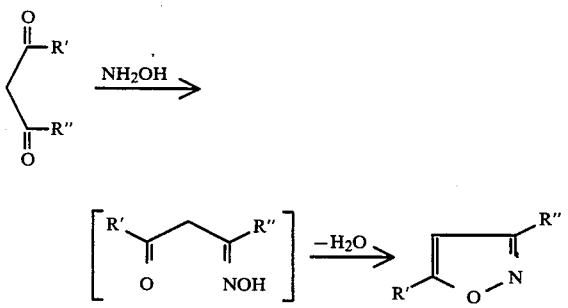

2. reacting alpha-acetylenic ketones or aldehydes with hydroxylamine in accordance with the following scheme:

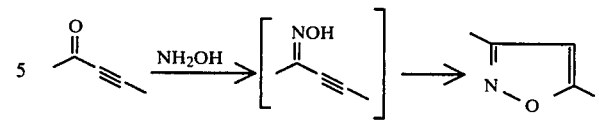

3. reacting halogenated alpha,beta-ethylenic ketones or aldehydes with hydroxylamine according to

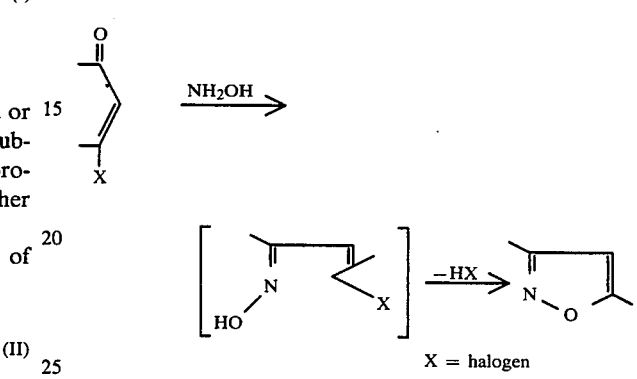

X = halogen or 4. reacting alpha,beta-unsaturated ketones with hydroxylamine

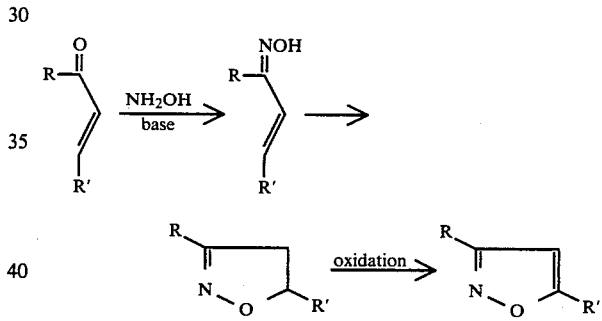

Swiss Pat. No. 553,207 discloses a process for the preparation of isoxazoles of formula

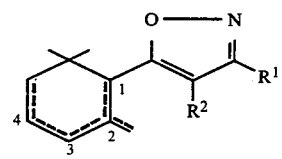

possessing an endocyclic double bond in position 1, 2, 3 or 4, or an exocyclic double bond in position 2, or two conjugated double bonds in positions 1 and 3 as indicated by the dotted lines and wherein $R^1$ and $R^2$ represent a lower alkyl radical or a hydrogen atom, which process is characterized in that an alpha,beta-unsaturated oxime of formula

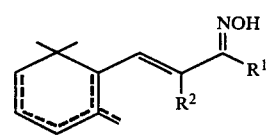

is cyclized by means of a stoichiometric amount of iodine, preferably in a neutral or alkaline aqueous medium. In order to maintain the required iodine in solution in the aqueous medium, it was suggested to add to it potassium iodide, that needed to be used in large excess (3 or 4 equivalents). The reagents employed are rather expensive and their use in the quantity considered renders the process uneconomical when applied to industrial scale production.

The instant invention provides a novel solution to this problem and proposes an electrochemical process which obviates the drawbacks of the prior known process.

PREFERRED EMBODIMENTS OF THE INVENTION

Symbol R in formula (I) can represent a linear or branched $C_1$-$C_6$ alkyl such as ethyl, propyl, n-butyl, iso-butyl, pentyl or hexyl; an unsaturated alkyl such as prop-1-en-1-yl, 2-methyl-prop-1-en-1-yl, 1-ethyl-pent-1-en-1-yl or 1-prop-hex-1-en-1-yl, for example; a cycloalkyl, for instance, 2,6,6-trimethylcyclohex-1-en-1-yl or 2,6,6-trimethyl-cyclohex-2-en-1-yl; or a phenyl or a 4-methoxy-phenyl.

The process of the invention is based on an anodic oxidation reaction of an alpha,beta-unsaturated oxime in the presence of the couple $I_2/2I^{-1}$. The process is characterized by a simple operative mode and offers several advantages over the prior known process of the art. In effect, the course of the reaction is easily monitored, the yields observed are good and the whole operation is perfectly reproducible, even under variable conditions of temperature, current intensity or reagents concentration. Consequently, its application and scale-up to industrial manufacture of isoxazole end-products is greatly facilitated.

The concentration of the starting material in the solution or electrolytic mixture is not particularly critical. However, we have found that too low concentrations reduce the overall efficiency of the operation, whereas too high concentrations tend to reduce the rate of the oxidation process in favor of secondary reactions, namely when the reaction is carried out in a heterogeneous medium. This phenomenon is but slightly perceptible in a homogeneous medium. Nonetheless, in both systems, it is preferred to operate with starting oxime concentrations lower than about 10% by weight.

Concerning the nature of the electrodes that can be used in the process of the invention, they can consist in graphite plates or platinum sheets for the anode or of platinum sheets or titanium plates, of MONEL (registered trademark) (nickel and copper alloy) or of nickel for the cathode. An anode of DSA type (registered trademark of Diamond Shamrock Technologies SA) of metal oxide on expanded metal form can also be employed.

A system consisting of an anode of graphite and a cathode of titanium was preferred.

The current intensity used was the order of about 10 to 50 mA/cm². However, the influence of this parameter on the course of the reaction is not determinant.

The reaction temperature can be of between about 25° and 70° C.; preferably, it is however of about the boiling temperature of the system chosen.

The process according to the invention can be effected in the presence of air, preferably however in an atmosphere of inert gas, e.g. nitrogen or argon.

As indicated above, the reaction can be carried out in the presence of sodium bicarbonate: a small amount of it is necessary and sufficient to achieve satisfactory results. Though the use of larger amounts did not have any positive influence on the yield observed, its absence leads to a serious slow-down of the reaction rate, accompanied by the formation of by-products of high molecular weight. In a homogeneous medium, 1 or 2% of sodium bicarbonate are usually sufficient.

The concentration of the alkali metal iodide, e.g. potassium iodide in the case of the reaction in heterogeneous phase or sodium iodide in the case of homogeneous phase, can vary within a wide range of values. In both cases, however, 30% by weight seem to be the minimum required concentration.

Concerning the proportion of tetrahydrofurane (THF) in the THF/H$_2$O mixture, in the case of a heterogeneous reaction, it has no critical effect. Consequently, it is preferred to operate with the most economical system, viz. with low THF concentrations. The presence of THF is however critical, without it in effect the reaction will be accompanied by the formation of a substantial amount of residue.

The process can be effected in a vessel possessing a sole electrolytic chamber or a separated one and it can proceed according to a batch or a continuous process; in this latter case, a tubular type cell can be conveniently used.

The invention is illustrated in more detals by but not limited to the following examples wherein the temperature areindicated in degrees centigrade and the abbreviations have the meaning common in the art.

EXAMPLE 1

3-Methyl-5-(2,6,6-trimethyl-cyclohex-1-en-1-yl)-isoxazole (method a.)

3.5 G (17 mM) of beta-ionone oxime of 97% purity were dissolved in 35 ml of tetrahydrofurane (THF) and the resulting solution was added to the aqueous solution constituted by 20 g of potassium iodide (120 mM) and 1 g (12 mM) of sodium bicarbonate in 15 ml of water.

The mixture, kept under argon atmosphere, was stirred and brought to the boil (ca. 65°) and a current density of B 50 mA/cm² was applied. The reaction was carried out in a standard three-neck vessel of 10 ml equipped with a normalized male teflon stopper bearing two electrodes placed at 1 cm distance each from the other. The vessel was equipped also with a condenser, a thermometer and a way in and out for the circulation of argon. The solution was magnetically stirred. The mixture became dark brown and the course of the reaction was followed by gas chromatographic analysis. After 4 hours of electrolysis, 90% conversion was achieved and the current was switched off and the reflux was maintained until discoloration of the mixture (2 to 3 hours). The whole quantity of oxime had then reacted. After cooling to reaction temperature, the organic phase was separated, dried and evaporated. The residue was distilled under reduced pressure (13.3 Pa) to give 2.9 g (14.5 mM) of the desired isoxazole at bp. 80°-85°. During the electrolysis, the pH of the solution increased slowly from 8.1 to 10.2 at which value it stabilized. The aqueous solution can be reutilized as such for the oxidation of a further charge of oxime in THF.

EXAMPLE 2

3-Methyl-5-(2,6,6-trimethyl-cyclohex-1-en-1-yl)-isoxazole (method b.)

The reaction was effected in an electrolysis vessel similar to that described in the previous example.

3.5 G of beta-ionone oxime (17 mM), 20 g of sodium iodide (133.0 mM) and 1 g (12 mM) of sodium bicarbonate were poured into 50 ml of methanol and the resulting mixture was brought to the boil (ca. 60°) under stirring and in an argon atmosphere. The electrolysis proceeded as described in Example 1 above by applying a current density of 50 mA/cm$^2$. After cooling to room temperature, solvent was stripped off and the viscous residue which resulted was diluted with 250 ml of toluene. In such a way, the sodium iodide, which was in solution, precipitated and was quantitatively recovered by filtration. The filtrate was then concentrated and the residue distilled in vacuum (13.3 Pa). 2.96 G (14.5 mM) of the desired isoxazole having bp. 80–85/13.3 Pa were obtained. Yield: 85%. The recovered sodium iodide could be utilized for successive electrolysis operation. The obtained isoxazole was in all respect identical with that described in U.S. Pat. No. 3,931,323.

By operating in an identical way to that described above, the following isoxazoles belonging to formula (I) were prepared starting from alpha,beta-unsaturated oximes of formula (II).

TABLE

| R | Eb.[°C./Pa] |
| --- | --- |
| 1. $CH_3$—$(CH_2)_3$ | 120/1.33 × 10$^3$ |
| 2. $(CH_3)_2$—CH—$(CH_2)_2$ | 130/1.33 × 10$^3$ |
| 3. $(CH_3)_2$—C≡CH | 145/1.33 × 10$^3$ |
| 4. $CH_3$—$(CH_2)_2$—CH=C—$C_2H_5$ | 110–130/1.33 |
| 5. $CH_3$—$(CH_2)_3$—CH=C—$C_3H_7$ | 92–99/1.33 |
| 6. $C_6H_5$ | 125/1.33 |
| 7. p-$CH_3O$—$C_6H_4$ | 101–103 (F) |
| 8. furyl | 170/1.33 × 10$^3$ |

The thus obtained isoxazoles showed the following analytical characteristics.

1. 3-methyl-5-butyl-isoxazole
IR (film): 2960, 1610, 1420 cm$^{-1}$.
NMR (360 MHz; $CDCl_3$): 0.93 (3H, t); 1.64 (2H, q); 1.88 (2H, sextuplet); 2.24 (3H, s); 2.70 (2H, t), 5.79 (1H, s) delta ppm.
MS: M$^+$=139 (20); m/e: 110 (8), 97 (100), 82 (25), 55 (57), 41 (24).

2. 3-methyl-5-(3-methylbutyl)-isoxazole
IR (film): 2990, 1620, 1460 cm$^{-1}$.
NMR (360 MHz; $CDCl_3$): 0.92 (6H, d); 1.55 (3H, m); 2.25 (3H, s); 2.70 (2H, t); 5.79 (1H, s) delta ppm.
MS: M$^+$=153 (2); m/e: 112 (28), 97 (100), 82 (33), 69 (29), 55 (78), 43 (58), 41 (56).

3. 3-methyl-5-(2-methylprop-1-en-1-yl)-isoxazole
IR ($CHCl_3$): 3000, 1665, 1593, 1587, 1420 cm$^{-1}$.
NMR (360 MHz; $CDCl_3$): 1.95 (3H, s); 2.01 (3H, s); 2.27 (3H, s); 5.90 (1H, s); 6.13 (1H, s) delta ppm.
MS: M$^+$=137 (100), m/e: 122 (7), 108 (10), 95 (39), 83 (63) 67 (48), 55 (85), 53 (41), 41 (37), 39 (68).

4. 3-methyl-5-(hept-3-en-3-yl)-isoxazole
IR (film): 2980, 1650, 1585, 1425 cm$^{-1}$.
NMR (360 MHz; $CDCl_3$): (isomer trans-): 0.94 (3H, t); 1.07 (3H, t); 1.48 (2H, sextuplet); 2.19 (2H, q); 2.27 (3H, s); 2.39 (2H, t); 5.94 (1H, s); 6.27 (1H, t) delta ppm.

NMR (360 MHz; $CDCl_3$): (isomer cis-): 0.94 (3H, t); 1.07 (3H, t); 1.48 (2H, s); 2.19 (2H, q); 2.31 (3H, s); 2.39 (2H, t); 5.19 (1H, t); 5.98 (1H, s) delta ppm.
MS: (isomer trans-): M$^+$=179 (44); m/e: 164 (6), 150 (38), 137 (100), 122 (33), 109 (35), 96 (51), 81 (79), 67 (36), 55 (49), 41 (57).
MS: (isomer cis-): M$^+$=179 (28); m/e: 164 (3), 150 (45), 137 (100), 122 (33), 109 (51), 96 (52), 81 (77), 67 (48), 55 (49), 41 (62).

5. 3-methyl-5-(non-4-en-4-yl)-isoxazole
IR (film): 2950, 1640, 1580, 1450, 780 cm$^{-1}$.
NMR (360 MHz; $CDCl_3$): (isomer trans-): 0.91 (3H, t); 0.93 (3H, t); 1.35–1.55 (3×2H, m); 2.21 (2H, q); 2.26 (3H, s); 2.35 (2H, t); 5.92 (1H, s); 6.41 (1H, t) delta ppm.
NMR (360 MHz; $CDCl_3$): (isomer cis-): 0.91 (3H, t); 0.93 (3H, t) 1.35–1.55 (3×2H, m); 2.21 (2H, q); 2.29 (3H, s); 2.35 (2H, t); 5.69 (1H, t) and 5.98 (1H, s) delta ppm.
MS: (cis=trans): M$^+$=207 (16); m/e: 178 (3), 164 (18), 151 (10), 136 (12), 123 (100), 110 (9), 95 (22), 82 (17), 67 (19), 55 (14), 41 (23).

6. 3-methyl-5-phenylisoxazole
IR ($CHCl_3$): 3040, 1610, 1600, 1580, 1420, 1210 cm$^{-1}$.
NMR (360 MHz; $CDCl_3$): 2.36 (3H, s); 6.35 (1H, s); 7.43 (3H, m); 7.75 (2H, m) delta ppm.
MS: M$^+$=159 (100); m/e: 130 (14), 116 (6), 105 (51), 89 (12), 82 (18), 77 (48), 63 (7), 51 (25).

7. 3-methyl-5-(4-methoxyphenyl)-isoxazole
IR ($CHCl_3$): 3010, 1620, 1515, 1255, 1175, 910 cm$^{-1}$.
NMR (360 MHz; $CDCl_3$): 2.33 (3H, s); 3.85 (3H, s); 6.24 (1H, s); 6.96 (2H, d), 7.69 (2H, d) delta ppm.
MS: M$^+$=189 (100); m/e: 174 (15), 160 (1), ;b 146 (18), 135 (49), 119 (11), 107 (8), 92 (15), 77 (24), 63 (13), 51 (10), 41 (4).

8. 3-methyl-5-(2-furyl)-isoxazole
IR ($CHCl_3$): 3000, 1643, 1545, 1450, 1415, 1010, 890, 790 cm$^{-1}$.
NMR (360 MHz; $CDCl_3$): 2.32 (3H, s); 6.26 (1H, s); 6.52 (1H, m); 6.84 (1H, d), 7.51 (1H, s) delta ppm.
MS: M$^+$=149 (100); m/e: 120 (2), 106 (4), 95 (43), 82 (32), 66 (18), 52 (15), 39 (18).

The beta-ionone oxime used as starting material in above examples 1 and 2 was prepared according to the process described in U.S. Pat. No. 3,931,323 (see in particular Example 3). In an analogous way, the other oximes of formula (II) were prepared from their corresponding ketones.

What we claim is:

1. A process for the preparation of isoxazoles of formula

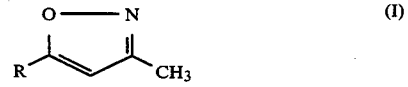

wherein R represents a linear or branched, saturated or unsaturated aliphatic radical, or a substituted or unsubstituted cycloaliphatic or aromatic radical, which process comprises subjecting to an anodic oxidation either
a. a two-layer heterogeneous mixture consisting of
(i) a solution in tetrahydrofuran of an alpha,beta-unsaturated oxime of formula

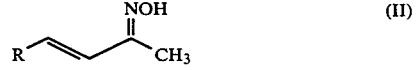

wherein symbol R possesses the meaning given above, and (ii) a solution of potassium iodide and sodium bicarbonate in water; or b. a homogeneous mixture consisting of a solution of said oxime of formula (II), sodium iodide and sodium bicarbonate in methanol.

2. A process according to claim 1 wherein the reaction is effected by using an anode of platinum or graphite.

3. A process according to claim 1 wherein the reaction is effected by using a cathode of titanium, nickel or an alloy of nickel-copper.

4. A process according to claim 1 wherein the reaction is effected by using a cathode of titanium and an anode of graphite.

5. A process according to any one of claims 1 to 4 wherein the oxime of formula (II) is present at a solution concentration equal or lower than 10% by weight.

6. A process according to any one of claims 1 to 4 wherein R is the same in formulae (I) and (II) and is (2,6,6-trimethyl-cyclohex-1-en-1-yl)-isoxazole.

7. A process according to claim 5 wherein R is the same in formula (I) and (II) and is (2,6,6-trimethyl-cyclohex-1-en-1-yl)-isoxazole.

* * * * *